United States Patent [19]

Hutchins et al.

[11] 4,244,884
[45] Jan. 13, 1981

[54] CONTINUOUS PROCESS FOR MAKING PEROXYCARBOXYLIC ACIDS

[75] Inventors: James P. Hutchins, Cincinnati; Dana C. Winn, Springdale, both of Ohio

[73] Assignee: The Procter & Gamble Company, Cincinnati, Ohio

[21] Appl. No.: 57,131

[22] Filed: Jul. 12, 1979

[51] Int. Cl.$^3$ ........................................... C07C 179/10
[52] U.S. Cl. ............................................. 260/502 R
[58] Field of Search ........................ 260/502 R, 502 A

[56] References Cited

U.S. PATENT DOCUMENTS

| | | | |
|---|---|---|---|
| 2,813,885 | 11/1957 | Swern et al. | 260/502 R |
| 2,813,896 | 11/1957 | Krim | 260/502 R |
| 2,814,641 | 11/1957 | Phillips et al. | 260/502 R |
| 2,816,147 | 12/1957 | Weber et al. | 260/502 R |
| 3,079,411 | 2/1963 | Silbert et al. | 260/502 R |
| 3,140,312 | 7/1964 | Kurhajei | 260/502 R |
| 3,143,562 | 8/1964 | Silbert et al. | 260/502 R |
| 3,284,491 | 11/1966 | Karoch et al. | 260/502 R |
| 3,655,738 | 4/1972 | Nielson | 260/502 R |
| 4,085,133 | 4/1978 | Briody | 260/502 R |
| 4,088,676 | 5/1978 | Hofen | 260/502 R |
| 4,119,660 | 10/1978 | Hutchins | 260/502 |
| 4,147,720 | 4/1979 | Berkowitz | 260/502 |

FOREIGN PATENT DOCUMENTS

| | | | |
|---|---|---|---|
| 864135 | 8/1978 | Belgium | 260/502 R |
| 744391 | 10/1966 | Canada | 260/502 R |

OTHER PUBLICATIONS

Parker et al. "Peroxides IV Aliphatic Diperacids".

*Primary Examiner*—Werren B. Lone

*Attorney, Agent, or Firm*—Ronald L. Hemingway; Richard C. Witte

[57] ABSTRACT

An improved continuous process for making a peroxyacid having about 6 to about 20, preferably about 8 to about 16 carbon atoms and at least one peroxyacid moiety, using as starting materials the corresponding carboxylic acid and hydrogen peroxide and using sulfuric acid as a reaction medium, comprising the steps of (a) maintaining a reaction mixture having a liquid component comprising 60 to 80% sulfuric acid, 2.5 to 12.5% hydrogen peroxide, and 7.5 to 37.5% water and a dispersed solid component comprising crystals of the carboxylic acid starting material and the peroxyacid product; (b) withdrawing a first recycle stream, which is filtered to remove the solid component and entrained liquid as a filter cake, leaving a liquid filtrate which is replenished with hydrogen peroxide, cooled to a temperature below the maximum permissible reaction temperature, and reinserted into the reactor; and (c) withdrawing a second recycle stream, which is replenished with sulfuric acid and with the carboxylic acid starting material, cooled to remove the heat of dilution of the sulfuric acid, and returned to the reactor; in order to continuously produce and remove from the site of reaction a filter cake from which a relatively pure peroxyacid is extracted, while maintaining in the reaction mixture the concentrations of each substance involved in the reaction. More generally, a continuous process in which solid reaction products and liquid side products are removed from a liquid-containing reaction medium while at least a portion of the liquid in said liquid-containing reaction medium is recycled to replenish the liquid-containing reaction medium.

11 Claims, 2 Drawing Figures

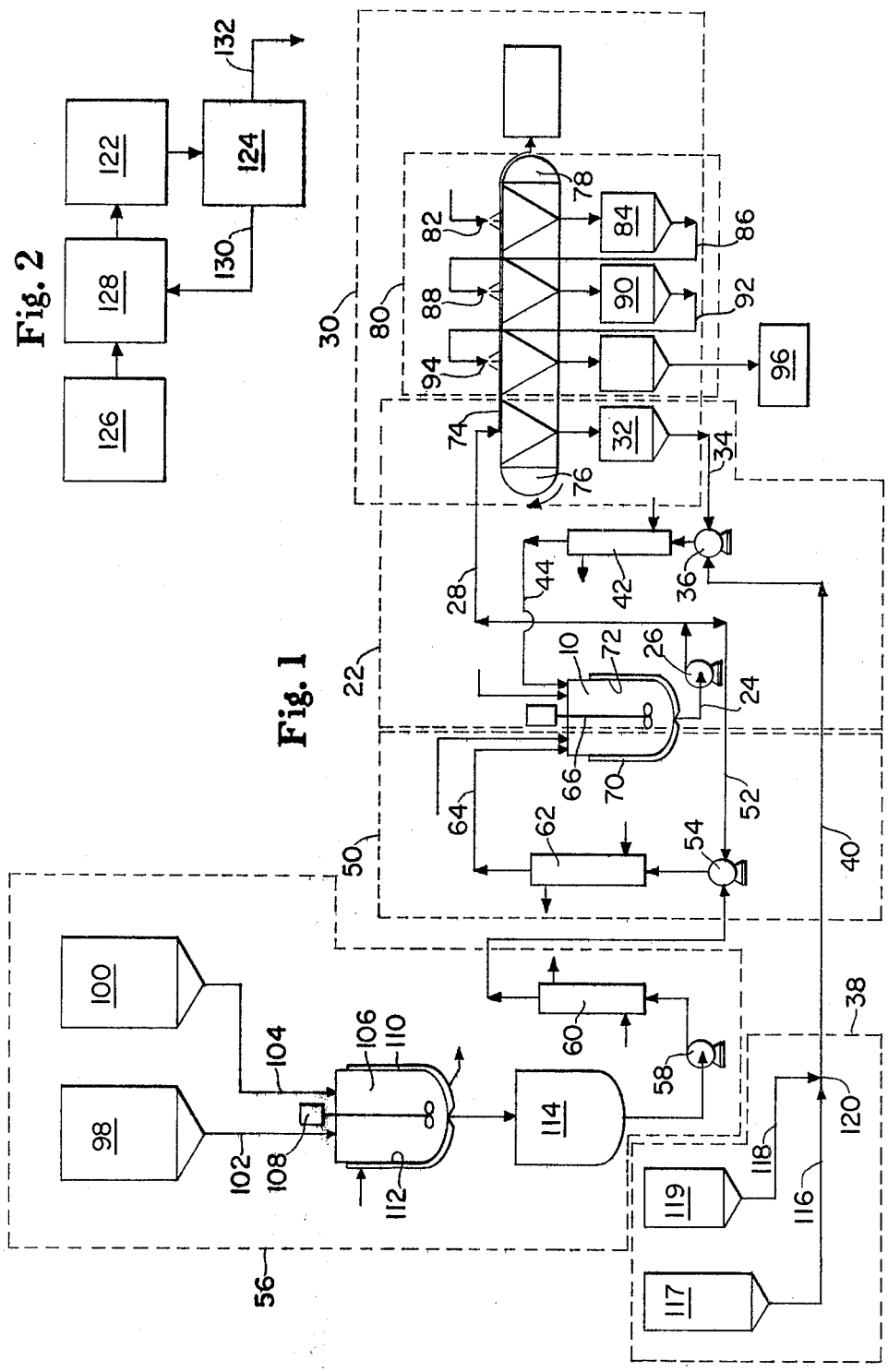

CONTINUOUS PROCESS FOR MAKING PEROXYCARBOXYLIC ACIDS

TECHNICAL FIELD

This invention relates to a continuous method for making crystalline peroxides of carboxylic acids from the corresponding carboxylic acid and hydrogen peroxide in a sulfuric acid reaction medium. More generally, this invention involves the separation of solid products and removal of liquid products from a liquid-containing reaction mixture in a continuous process while providing for recycling of the liquid portion of the liquid-containing reaction mixture.

BACKGROUND ART

The following documents disclose continuous processes for producing peroxyacids or the like from hydrogen peroxide, sulfuric acid, and a carboxylic acid: U.S. Pat. No. 2,816,147, issued to Weber et al. on Dec. 10, 1957; U.S. Pat. No. 3,140,312, issued to Kurhagec et al. on July 7, 1964; U.S. Pat. No. 4,087,455, issued to Prescher et al. on May 2, 1978; Canadian Pat. No. 744,391, issued to Wenzke et al. on Oct. 11, 1966; and U.S. Ser. No. 895,411, filed by Camden et al. on Apr. 11, 1978 (the latter application is owned by the owners of the present application).

The Wenzke reference is distinguishable because it teaches the production of lower aliphatic peroxyacids which are removed from the reaction vessel by distillation, while in the present invention the peroxyacid must be solid in order to be removed by filtering, as will be disclosed in more detail hereinafter. The Weber reference provides for separate cooling of two reactant streams before mixing them in the reactor but does not allow for any predilution of the reactants with reactor contents. The Kurhagec reference alleges a continuous process for producing peroxyacids, but the specification of that reference does not teach how to adapt the disclosed batch processes to continuous operation. The Camden case includes a brief description of the present invention which was inserted as a description of the best mode of practicing that invention, but the disclosure embodied therein is the invention of the present inventors and is not seen to be prevented by any statutory bar from being claimed in the present application.

The Prescher reference teaches that a peroxyacid product may be removed from the reaction mixture by extracting reactor effluent with an organic solvent, followed by the steps of mixing the resulting raffinate with fresh peroxide solution, distilling the raffinate to remove water, and reinserting the raffinate into the reactor. The Prescher reference is distinguishable from the present invention in several respects, including the requirements in Prescher of a separate distilling step to remove water from the reaction mixture and the apparent need in Prescher to remove the peroxyacid from an organic solvent in which it would necessarily be dissolved in the process of performing the required solvent extraction. The Prescher process also does not provide for the predilution of reactants with reactor contents in order that the heat of dilution of the reactants may be largely dissipated before the reactants are introduced into the reactor.

Numerous prior art references indicate the problem in the prior art of performing the present reaction safely, since if the reaction is not carefully controlled it can become uncontrollable, resulting in an exothermic reaction or even an explosion, or at least in an obstruction of the passages of the reaction apparatus.

DISCLOSURE OF INVENTION

The inventors have discovered the following process for continuously making a peroxyacid having about 6 to about 20, preferably about 8 to about 16 carbon atoms and at least one peroxyacid moiety, preferably such a compound with a peroxyacid moiety on each terminal carbon atom of an aliphatic straight-chain hydrocarbon moiety, and more preferably diperoxydodecanedioic acid. This product is produced as follows: a reaction mixture comprising a liquid phase and a filterable solid phase is maintained in a continuously stirred tank reactor with two recycling loops. The liquid phase of the reaction mixture comprises 60 to 80% by mixture weight concentrated sulfuric acid, 2.5 to 12.5% by mixture weight pure hydrogen peroxide, and 7.5 to 37.5% by mixture weight water. In a preferred mode of practicing the invention, this liquid phase comprises 70 to 77% by mixture weight sulfuric acid, 2.5 to 7.5% by mixture weight hydrogen peroxide, and 15.5 to 27.5% by mixture weight water. Most preferably, the liquid phase of the invention slurry comprises 71 to 75% by mixture weight sulfuric acid, 4.5 to 7.5% by mixture weight hydrogen peroxide, and 17.5 to 24.5% by mixture weight water. The filterable solid phase of the reaction mixture comprises the peroxyacid reaction product and the carboxylic acid reactant. (In one mode of the invention the solid phase is comprised of 92% peroxyacid and about 8% carboxylic acid starting material, although these percentages are not critical to the present invention.)

The continuously stirred tank reactor system has a first recycle loop in which a portion of the reaction slurry is filtered to remove the filterable solid phase (filter cake), forming a filtrate. The filtrate is replenished with hydrogen peroxide solution to form a replenished filtrate stream, the replenished filtrate stream is passed through a heat exchanger in order to cool it and to thus moderate the temperature within the reaction vessel, and the replenished filtrate stream is then returned to the stirred reactor. Water of reaction is also removed from the system in this recycle loop, for sufficient water is in the solution entrained on the filter cake to compensate for water of reaction and for water which is added in the form of a diluent for the hydrogen peroxide solution. (In further steps not forming a part of this invention the filter cake is dried to produce a relatively pure peroxyacid product which may then be incorporated into a bleaching composition.)

The reactor also desirably contains a second recycle loop in which a portion of the reaction slurry removed from the reactor is blended with the sulfuric acid and carboxylic acid starting materials. The reaction slurry is passed through a heat exchanger in order to dissipate the heat of dilution, especially the heat of dilution of the sulfuric acid, and is then returned to the reactor.

This reaction scheme allows the introduction of the sulfuric acid and carboxylic acid starting materials at a location remote from the site of introduction of the hydrogen peroxide starting material in order to prevent the production of localized areas of high reactant concentrations which are capable of initiating an uncontrolled reaction. The temperature of the entire reaction mixture is also controlled by eliminating the heat of dilution and some of the heat of the reaction outside of the reactor in order to minimize the amount of heat which must be removed from within the reaction vessel. The reaction is carried out in the stirred reaction vessel at a temperature between about 15° C. and 45° C., preferably 15° C. to 35° C., and more preferably 32° C. to 35° C.

It has been found that the ratio of the weight of the liquid phase to the weight of the solid phase in the reaction mixture must be at least about 3:1, and is preferably between 8:1 and about 50:1, in order to carry out the present invention. (It should be noted that the solid phase includes most of the carboxylic acid starting material, even though this material is added to the reaction mixture in the form of a solution in sulfuric acid. The carboxylic acid typically precipitates after the solution of carboxylic acid in sulfuric acid is added to the balance of the reaction mixture.)

In its broadest aspect the inventors consider their invention to be a method of conducting a continuous reaction wherein liquid products and solid products are continuously removed from a slurry comprising: (i) liquid products, (ii) solid products, and (iii) at least one additional liquid component, comprising the steps of: (a) filtering a portion of said slurry to remove the solid products, as well as portions of the liquid products and of at least one additional liquid component entrained by the solid product, thereby forming a filtrate; (b) recycling said filtrate into the balance of said slurry; and (c) adding to said slurry sufficient quantities of at least one additional liquid component to replace the portion thereof entrained on said solid product; whereby the capacity of said solid products to entrain a mixture of said liquid products and liquid component is sufficient to entrain the liquid products at least as fast as they are formed in or added to the reaction mixture.

DESCRIPTION OF THE DRAWINGS

FIG. 1 is a schematic flow diagram of a preferred mode of practicing the present invention.

FIG. 2 is a flow diagram of the broadest aspect of the present invention.

DETAILED DESCRIPTION OF THE INVENTION

A preferred mode of practicing the invention is illustrated in FIG. 1.

The reaction takes place in continuously stirred tank reactor 10. The first recycle loop of the reactor is indicated generally by reference character 22. A portion of the contents of reactor 10 passes through exit conduit 24 and is conveyed by pump 26 and conduit 28 to filtering and washing means indicated generally by reference character 30, where the filter cake is removed from the filtrate and washed to produce a finished product. The filtrate passes through filter belt 74, collects in filtrate collector 32 and passes through conduit 34 to pump 36. At this point hydrogen peroxide solution from $H_2O_2$ supply means generally indicated by reference character 38 is conveyed through conduit 40 to join the contents of conduit 34 substantially within pump 36. The combined stream then passes through heat exchanger 42 which removes the heat of dissolution and some heat of reaction of the mixture. The mixture is then returned to reactor 10 through conduit 44. Thus, in first recycle loop 22 reaction products are removed, the hydrogen peroxide contents of the reactor are replenished, and the heats of reaction and of dilution which are generated when the hydrogen peroxide stream is combined with the filtrate stream are dissipated.

The second recycle loop, generally indicated by reference character 50, functions as follows: A portion of the reactor contents is conveyed through exit conduit 24 and pump 26 as before, then through conduit 52 to pump 54. The carboxylic acid/sulfuric acid solution supply means, generally indicated by reference character 56, supplies a solution of sulfuric acid and the carboxylic acid starting material via pump 58 and heat exchanger 60 to pump 54, where the carboxylic acid/sulfuric acid solution is combined with a portion of the contents of reactor 10. After the reaction mixture is replenished with the carboxylic acid/sulfuric acid solution, the carboxylic acid largely precipitates to become a part of the solid phase of the slurry. The mixture, combined substantially within pump 54, is then passed through heat exchanger 62 in order to remove the heats of reaction and dilution generated by the mixture of the streams and the mixture is then conveyed via conduit 64 to reactor 10. Thus, in second recycle loop 50 reactor contents are combined with a solution of the carboxylic acid starting material in sulfuric acid, the combination is cooled to remove heats of dilution and of reaction, and the resulting mixture is returned to the reactor 10, replenished with respect to sulfuric acid and the carboxylic acid starting material.

The construction and function of each component in FIG. 1 will now be discussed in greater detail.

Reactor 10 is a continuously stirred tank reactor of conventional construction. Reactor 10 is provided with stirring means 66 to continuously blend the ingredients in the reactor. It will be understood by those skilled in the art that many may be used to stir the contents of the reactor. For example, if the reactor contents are rapidly recycled through second recycle loop 50, adequate stirring will in some cases be provided for the reaction. It is important, however, that adequate stirring be provided to prevent the formation of localized pockets having unduly high concentrations of reactants, for otherwise uncontrolled localized exothermic reactions may occur. Reactor 10 is further provided with a cooling jacket 70, which is desirable in order to minimize the temperature of the reactor contents to maintain the desired temperature range of 15° C. to 45° C., preferably 25° C. to 40° C., and more preferably 32° C. to 35° C. Reactor 10 has an interior wall 72, which may be made of any material which is nonreactive with the reactor contents. In an especially preferred embodiment of the invention, interior wall 72 may be made of glass or tantalum, or may be a TEFLON coating on a suitable substrate. (TEFLON is a trade name for certain polytetrafluoroethylene polymers sold by the E. I. DuPont de Nemours Company.) Other materials for interior wall 72 will suggest themselves to those skilled in the art, although it should be noted that stainless steel is a less preferred material for interior wall 72 because it has been found that stainless steel which is allowed to come in contact with the reaction mixture leaves a residue in the products of reaction which later hastens the decomposition of the peroxyacid product formed by this process.

As shown in FIG. 1, filtering and washing means 30 may be a belt filter of the type having a countercurrent rinse. Filtering and washing means 30 comprises an endless moving filter belt 74 which may be a foraminous belt made of polypropylene or polyethylene. Filter belt 74 is carried on pulleys 76 and 78, at least one of which is driven in order to induce the endless motion of filter belt 74. It will be appreciated that idler rolls and like means may be provided intermediate pulleys 76 and 78 in order to lend further support to the filter belt 74. The belt, in this embodiment of the invention, travels at a surface speed of 1.7 feet per minute (0.86 centimeters per second). The structure generally indicated by reference character 80 is a countercurrent rinse, which in this embodiment is shown as a three-stage rinse system. The rinsing medium, typically water, forms shower 82, which impinges upon the right side of filter belt 74 and the solid material carried thereon. The wash medium proceeds through filter belt 74 and is collected in reservoir 84. The liquid contained in reservoir 84 is then passed via conduit 86 and associated liquid transport means (not shown) to form shower 88. Shower 88 impinges on filter belt 74 and the solid product contained thereon, passes through filter belt 74, and is collected in reservoir 90. In similar fashion the contents of reservoir 90 pass via conduit means 92 to form shower 94, which passes through filter belt 74 and the solid product supported thereon. The spent rinse medium is collected in rinse disposal means 96 and may thereafter be discarded.

It will be appreciated, because the travel of solid product on filter belt 74 is shown here as being from left to right, and because the countercurrent rinse medium successively washes from right to left with respect to filter belt 74, that in the first rinsing step in this embodiment of the invention the fresh rinsing medium passes through relatively well-rinsed product, while successively more spent rinse media pass through the successively less well-rinsed portions of the reaction product carried on the central sections of the belt as shown in FIG. 1. It will be appreciated by those skilled in the art that this mode of rinsing provides for the most efficient use of the rinse medium to purify the reaction product. It will also be appreciated by those skilled in the art that the rinse medium may contain any of a number of agents which will increase its effectiveness. For example, the rinse medium may contain an alkaline salt such as sodium hydroxide which is effective to neutralize the residue of sulfuric acid which is entrained on the solid reaction product. A portion of filter belt 74 adjacent pulley 76 is the site where the reactor contents are passed through belt 74 in order to deposit the solid contents of the reactor on filter belt 74. A portion of of the liquid components of the reaction mixture pass through filter belt 74 and collect in filtrate collector means 32. The filtrate is further processed as indicated in the above description, and is then returned to reactor 10. It will be noted that the solid product deposited on belt 74 comprises 1 part by weight of solid material, in which is entrained approximately 3 parts by weight of liquid reaction components.

Heat exchangers 42, 60, and 62 may be of any conventional design, and in this embodiment are tube and shell exchangers. The heat exchangers are preferably lined with, or made of, a material which is inert with respect to the components of the present reaction. Preferred materials for use in the reaction-containing portions of these heat exchangers are TEFLON and tantalum.

In the embodiment of the present invention shown in FIG. 1, solution supply means 56 comprises storage means 98 which contain the carboxylic acid starting material, storage means 100 which contain concentrated sulfuric acid, and supply means 102 and 104 which respectively carry the carboxylic acid of storage means 98 and the sulfuric acid of storage means 100 to mixing tank 106. Mixing tank 106 includes stirring means 108 which dissolve the carboxylic acid in the sulfuric acid to form a true solution. In a preferred embodiment of the invention, mixing tank 106 has a water jacket 110 which serves to heat the carboxylic acid/sulfuric acid solution to hasten the dissolution of the carboxylic acid in the sulfuric acid. Interior wall 112 of mixing tank 106 may be made of any suitable material which is inert to the carboxylic acid and to sulfuric acid, especially TEFLON or a TEFLON coating on a suitable substrate. The solution which is made in mixing tank 106 is conveyed to storage tank 114, from which the slurry is drawn as it is needed in the reaction. It will be appreciated that this particular embodiment of solution supply means 56 does not in any way limit the invention, and in fact any means of supplying the solution to the reaction and of maintaining an adequate supply of the solution on hand to maintain the reaction may be substituted for the indicated solution supply means.

Hydrogen peroxide supply means 38 is, in this embodiment of the invention, comprised of a supply 117 of concentrated hydrogen peroxide, which may contain from 25% to 90% hydrogen peroxide in water by weight, water supply means 119 which supplies distilled water, supply conveying and conduit means 116 and 118, and mixing zone 120 where sufficient quantities of water and of hydrogen peroxide are brought together to form in combination a mixture containing about 30% to 70% hydrogen peroxide in water by weight. The specific structure of the hydrogen peroxide supply means shown in FIG. 1 is not critical to the present invention, and any means of supplying a solution of 30% to 70% by weight hydrogen peroxide in water to the reaction apparatus is adequate to the task.

Pumps 54 and 26 are preferably low shear pumps which are especially adapted to avoid breaking up the crystals of peroxyacid product which are contained in the reaction slurry which they pump. All of the other pumps shown in FIG. 1 are of conventional design, although it will be noted that the pump surfaces which contact the reaction mixture or components must be made of a material which is essentially inert to the materials which they pump, as will be appreciated by those skilled in the art. The rate of pumping in the several conduits of the reactor is adjusted with respect to the size of the reactor so that the average residence time of the reaction components in the reactor is about 0.25 to 1.5 hours, preferably 0.5 to 1.0 hours.

In a preferred mode of the present invention, every surface of the apparatus of FIG. 1 which is allowed to come in contact with the reaction components, product, or incoming ingredients is inert to the ingredients with which these surfaces come in contact in order to prevent the occurrence of side reactions which frequently are found to precipitate an exothermic reaction or to hasten the degradation of the peroxyacid products produced according to the present process. In particular, these problems are observed to a limited degree when stainless steel is used as the surface with which reaction components or products come into contact.

Another particularly preferred feature of the present process for producing solid peroxyacids is the provision for removal of the water of reaction and of the water of dilution for the hydrogen peroxide in a particularly simple and efficient manner.

The equilibrium reaction which forms the basis for the present process proceeds according to the following formula:

$$R(COOH)_x + X\ H_2O_2 \xrightleftharpoons{H_2SO_4} R(CO_3H)_x + X\ H_2O$$

where R is an organic moiety and X is an integer. Since this is an equilibrium reaction, in the present continuous process it is necessary to continuously remove the water of reaction and of dilution, as well as the peroxyacid product as it is formed, in order to drive the reaction toward completion. In the present process this is accomplished without an organic solvent extraction step, and without requiring that the reaction mixture be distilled in order to separate the water of reaction and of dilution from the reaction products. In practicing the present development it has been found that the solid peroxyacid product which is deposited on filter belt 74 entrains several times its weight of the liquid components of the reaction mixture—of course, the exact amount entrained will depend on the mode of filtering which is employed, the crystal size and distribution, and other factors. Using the filtering means described above, the filtered solid product contains roughly 3 times its weight of entrained liquid. As will become evident in the specific examples of operation of the present process which are set forth hereinafter, the reaction conditions can be adjusted so that the amount of water in the entrained liquid reaction components is essentially equal to the amount of water which is added via water supply reservoir 119, hydrogen peroxide solution reservoir 117, and which is formed as water of reaction due to consumption of hydrogen peroxide. Thus, provided that the process is run under such conditions that the material balance of incoming water and water of reaction is equal to the outgoing balance of entrained water, it is possible to maintain the proportion of water in the liquid portion of the reaction mixture at an essentially constant level.

The adjustment of the percentages of sulfuric acid and hydrogen peroxide in the liquid portion of the reaction mixture is more straightforward. The sulfuric acid is merely replaced as fast as it is removed from the reaction slurry as liquid entrained on the solid product, since sulfuric acid is neither created nor destroyed during the course of the present invention. The amount of the carboxylic acid starting material which is added to the reaction mixture is adjusted to be just sufficient to replace the carboxylic acid starting material which is used up in the course of the reaction, plus the small amount, typically less than 10%, of carboxylic acid starting material which remains in the reaction mixture at the time the mixture is filtered. Since the preferred carboxylic acid starting materials of the present invention are solids, it will be apparent that filter belt 74 will typically collect the residue of any of the preferred carboxylic acid starting materials. Likewise, the hdyrogen peroxide which is consumed in the reaction or entrained in the filter cake is replaced in equal amount in the continuous process in order to maintain the concentration of hydrogen peroxide at the claimed levels.

FIG. 2 depicts a reaction flow diagram which amplifies and generalizes the first recycle stream of the peroxyacid reaction to an embodiment of broad applicability which is useful whenever a reaction is carried out in which solid products are formed in a liquid-containing reaction medium. The required components of this process are reactor 122, filter 124, reactant supply means 126, and manifold 128. Contents of reactor 122 are passed through filter means 124 and thus divided into a filtrate stream 130 and a filter cake stream 132. Filtrate stream 130 is mixed with at least one reactant from reactant supply 126 in manifold 128. Manifold 128 may be simply the juncture of two inputs and one output, as in a tee joint, although more complex means are also contemplated within the scope of the present invention. The resulting replenished recycle stream is then returned to reactor 122.

In any reaction scheme in which a crystalline solid product and liquid by-products are formed in a liquid-containing reaction medium, if the filter cake is capable of entraining sufficient of the liquid components to remove the liquid by-products from the reaction as they are formed in the reaction or added to the reaction mixture, the material balance of the reaction will be such as to allow the liquid product to be removed concurrently with the solid product while a portion of the reacting mixture is recycled to conserve components of the reaction. A person skilled in the art will find it possible to adapt this process to a great number of different reactions in which solid and liquid products are concurrently produced in a medium with a liquid component which is recyclable.

Reaction Medium

While in the preceding description of the invention sulfuric acid is the only reaction medium and catalyst described, those skilled in the art will find this invention to be readily adaptable to the use of other reaction media. Specific examples of alternate reaction media useful herein are methanesulfonic acid, phosphonic acid, and pyrophosphoric acid.

Reaction Composition

The carboxylic acids which are useful as starting materials in the present invention are organic acids having from about 6 to about 20, preferably about 8 to about 16 carbon atoms (especially from 11 to about 16 carbon atoms) and at least one carboxylic acid moiety. Preferred reactants are straight-chain aliphatic carboxylic acids having a carboxylic acid moiety on each of the terminal carbon atoms of the chain.

Specific examples of monocarboxylic acids which are useful in the practice of the present process are as follows: hexanoic (caproic) acid, heptanoic (enanthic) acid, octanoic (caprylic) acid, nonanoic (nonylic, pelargonic) acid, decanoic (capric, decyclic) acid, undecanoic (hendecanoic, undecyclic) acid, dodecanoic (lauric) acid, tridecanoic acid, tetradecanoic (myristic) acid, pentadecanoic (pentadecylic) acid, hexadecanoic (palmitic) acid, haptadecanoic (margaric) acid, octadecanoic (stearic) acid, nonadecanoic (nonadecyclic) acid, and eicosanoic (arachic) acid. It will also be appreciated that mixtures of the above carboxylic acids are useful as starting materials in the present invention.

Examples of especially preferred carboxylic acid reactants of the present invention are the following dicarboxylic acids: 1,6-hexanedioic (adipic) acid, 1,7-hepanedioic (pimelic) acid, 1,8-octanedioic (suberic) acid, 1,9-nonanedioic (azelaic) acid, 1,10-decanedioic (sebacic) acid, 1,11-undecanedioic acid, 1,12-dodecanedioic acid, 1,13-tridecanedioic acid, 1,14-tetradecanedioic acid, 1,15-pentadecanedioic acid, 1,16-hexadecanedioic acid. 1,17-heptadecanedioic acid, 1,18- octadecanedioic acid, 1,19-nonadecanedioic acid, and 1,20-eicosanedioic acid. 1,12-dodecanedioic acid is the most preferred reactant. Other, similar peroxyacids may be used as reaction starting materials, provided that their corresponding peroxyacid products are solids which are relatively insoluble in the reaction mixture. Again, mixtures of the above materials are within the scope of the reactants which may be used to practice the present invention, as are mixtures of mono- and dicarboxylic acids.

The products which are formed as a result of the present process are peroxyacids corresponding to the carboxylic acid starting materials listed above. The product of the reaction may be a peroxyacid comprising a compound of 6 to 20 carbon atoms and at least one peroxyacid moiety, specifically, peroxyhexanoic acid, peroxyheptanoic acid, peroxyoctanoic acid, peroxynonanoic acid, peroxydecanoic acid, peroxyundecanoic acid, peroxydodecanoic acid, peroxytridecanoic acid, peroxytetradecanoic acid, peroxypentadecanoic acid, peroxyhexadecanoic acid, peroxyheptadecanoic acid, peroxyoctadecanoic acid, peroxynonadecanoic acid, or peroxyeicosanoic acid.

Preferred products are straight-chain aliphatic compounds having 8 to 16 carbon atoms and a peroxyacid moiety on each terminal carbon atom. The preferred products produced according to the present process are 1,6-diperoxyhexanedioic acid, 1,7-diperoxyheptanedioic acid, 1,8-diperoxyoctanedioic acid, 1,9-diperoxynonanedioic acid, 1,10-diperoxydecanedioic acid, 1,11-diperoxyundecanedioic acid, 1,12-diperoxydodecanedioic acid, 1,13-diperoxytridecanedioic acid, 1,14-diperoxytetradecanedioic acid, 1,15-diperoxypentadecanedioic acid, 1,16-diperoxyhexadecanedioic acid, 1,17-diperoxyheptadecanedioic acid, 1,18-diperoxyoctadecanedioic acid, 1,19-diperoxynonadecanedioic acid, and 1,20-diperoxyeicosanedioic acid.

The diperoxyacids may be characterized by the following formula, where n may be 4 to 18 inclusive, preferably 6 to 14 inclusive (especially 9 to 14 inclusive):

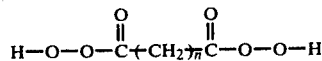

The most preferred reaction product is 1,12-diperoxydodecanedioic acid.

The indicated diperoxyacid products have utility as bleaching agents.

EXAMPLE

The following is an example of operation of the present process in a continuous mode to produce peroxyacids under constant and safe conditions. This example is provided not to limit the scope of the invention but to illustrate a preferred mode of practice of the invention.

In this example the apparatus was constructed as shown in FIG. 1 of the specification. Continuously stirred tank reactor 10 was a 30 gallon (114 liter) capacity glass-lined reaction vessel. Filter means 30 was a straight-line horizontal vacuum filter with an effective surface area of 3 square feet (0.28 square meters), utilizing a foraminous filter made of polypropylene and having a mesh size of roughly 32 filaments per inch (12.6 filaments per centimeter). Filter means 30 drew a vacuum of 22 inches (559 mm.) of mercury. Pump 26 was a plastic diaphragm pump capable of pumping at a rate of at least 20 gallons per minute (76 liters per minute). Heat exchanger 62 was a TEFLON heat exchanger having an effective surface area of 80 square feet (7.4 square meters) and an approximate capacity of 50,000 BTU (12,600 kg-cal.) per hour. Heat exchanger 42 was a jacketed 50 gallon (189 liter) Pflauder reactor provided with means to stir the contents thereof. Heat exchanger 42 had an effective surface area of 10 square feet (0.93 square meters) and a capacity of 5,000 BTU (1,260 kg-cal.) per hour. Each heat exchanger was cooled with water. Mixing tank 106 contained a solution comprising 26% dodecanedioic acid in concentrated sulfuric acid. The hydrogen peroxide solution formed at mixing zone 120 was a 50% solution of hydrogen peroxide in water. In this example the contents of continuously stirred tank reactor 10 were maintained with a liquid composition of 75% by weight sulfuric acid, 5.5% by weight hydrogen peroxide, and 19.5% water. The slurry in continuously stirred tank reactor 10 further contained a dispersed solid phase comprising approximately 10% carboxylic acid starting material (dodecanedioic acid) and 90% diperoxydodecanedioic acid. The ratio of solid to liquid components in the reaction slurry was about 1:10.

The reaction apparatus was prepared to begin continuous operation by charging the continuously stirred reaction vessel 10 with a mixture of reactants and products which were equivalent to the reactor contents to be maintained throughout the reaction process. Thus, the reaction vessel 10 was initially charged with 10 parts of a liquid composition comprising roughly 75% sulfuric acid, 5.5% hydrogen peroxide, and 19.5% water, combined with 1 part of diperoxydodecanedioic acid dispersed in the crystalline form. Stirring means 66 were immediately activated in order to maintain the dispersion of the reaction mixture. At the same time the flow of the carboxylic acid starting material through supply means 102 and of the sulfuric acid starting material through supply means 104 was begun, whereby the carboxylic acid/sulfuric acid solution was formed in mixing tank 106 and conveyed to solution storage tank 114, while tanks 98, 100, 117, and 119 were maintained with an adequate supply of the respective carboxylic acid, sulfuric acid, hydrogen peroxide solution, and water starting materials. Pump 26 was then started to begin the flow of material through recycle loops 1 and 2. The remaining pumps were then started up in order to maintain the flow of reactants, reaction mixtures, and recycled products. When the reaction reached a steady state of operation, the reaction temperature in reaction vessel 10 was approximately 35° C., the temperatures of the incoming streams entering the reactor were less than 35° C., 148 lbs. (67 kg.) per hour of the filtrate were produced, the filter cake contained 25 lbs. (11.3 kg.) per hour of diperoxydodecanedioic acid and 2 lbs. (0.91 kg.) per hour of the carboxylic acid starting material, as well as 35 to 100 lbs. (15.9 to 45.4 kg.) per hour of the entrained reaction solution. The second recycle loop conveyed 15 to 20 gallons (57 to 76 liters) per minute of the reaction mixture. 50% hydrogen peroxide solution was supplied to reaction vessel 10 at the rate of 21 lbs. (9.53 kg.) per hour, and a solution of 26% dodecanedioic acid in sulfuric acid was supplied to the second recycle stream at a rate of 89.5 lbs. (40.6 kg.) per hour.

COMPOSITIONS CONTAINING THE PEROXYACID COMPOUNDS

The peroxyacid compounds made using the process of the present invention can be used in a wide variety of compositions. A preferred use, especially of diperoxydodecanedioic acid, is as a fabric bleaching agent. To insure that compositions containing the peroxyacid compounds are safe and effective, certain additives are desirably present.

It is well documented in the literature that peroxyacids are susceptible to a number of different stability problems, as well as being potentially hazardous compounds. Looking at the latter first, peroxyacids decompose exothermally and when the material is in dry granular form the heat generated must be controlled to make the product safe. The best exotherm control agents are those which are capable of liberating moisture at a temperature slightly below the decomposition temperature of the peroxyacid employed. U.S. Pat. No. 3,770,816, Nov. 6, 1973, to Nielsen, incorporated herein by reference, discloses a wide variety of hydrated materials which can serve as suitable exotherm control agents. Included among such materials are magnesium sulfate .7H$_2$O, magnesium formate dihydrate, calcium sulfate (CaSO$_4$.2H$_2$O), calcium lactate hydrate, calcium sodium sulfate (CaSO$_4$.Na$_2$SO$_4$.2H$_2$O), and hydrated forms of, for example, sodium aluminum sulfate, potassium aluminum sulfate, ammonium aluminum sulfate and aluminum sulfate. Preferred hydrates are the alkali metal aluminum sulfates; particularly preferred is potassium aluminum sulfate. Other preferred exotherm control agents are those materials which lose water as the result of chemical decomposition such as boric acid, malic acid and maleic acid. The exotherm control agent is preferably used in an amount of from about 100% to about 200% based on the weight of the peroxyacid compound.

The other problems faced when peroxyacid compounds are used fall into the area of maintaining good bleach effectiveness. It has been recognized that metal ions are capable of serving as catalyzing agents in the degradation of the peroxyacid compounds. To overcome this problem chelating agents can be used in an amount ranging from 0.005% to about 1.00% based on the weight of the composition to tie up heavy metal ions. U.S. Pat. No. 3,442,937, May 6, 1969, to Sennewald et al., discloses a chelating system comprising quinoline or a salt thereof, an alkali metal polyphosphate and, optionally, a synergistic amount of urea. U.S. Pat. No. 2,838,459, June 10, 1958, to Sprout, Jr., discloses a variety of polyphosphates as stabilizing agents for peroxide baths. These materials are useful herein as stabilizing aids. U.S. Pat. No. 3,192,255, June 29, 1965, to Cann, discloses the use of quinaldic acid to stabilize percarboxylic aids. This material, as well as picolinic acid and dipicolinic acid, would also be useful in the compositions of the present invention. A preferred chelating system for the present invention is a mixture of 8-hydroxyquinoline and an acid polyphosphate, preferably acid sodium pyrophosphate. The latter can be a mixture of phosphoric acid and sodium pyrophosphate wherein the ratio of the former to the latter is from about 0.5:1 to about 2:1 and the ratio of the mixture to 8-hydroxyquinoline is from about 1:1 to about 5:1.

In addition to the above-mentioned chelating systems to tie up heavy metals in the peroxyacid compositions, coating materials may also be used to extend the shelf life of dry granular compositions. Such coating materials may be, in general, acids, esters, ethers and hydrocarbons and include such things as wide varieties of fatty acids, derivatives of fatty alcohols, such as esters and ethers, derivatives of polyethylene glycols, such as esters and ethers, and hydrocarbon oils and waxes. These materials aid in preventing moisture from reaching the peracid compound. Secondly, the coating material may be used to segregate the peracid compound from other agents which may be present in the composition and adversely affect the peracid's stability. When used in this manner the coating may be used on both the peracid compound and the other agent or either individually. The amount of the coating material used is generally from about 2.5% to about 15% based on the weight of the peroxyacid compound.

Additional agents which may be used to aid bleaching performance include pH adjustment agents, bleach activators and minors such as coloring agents, dyes and perfumes. Typical pH adjustment agents are used to alter or maintain aqueous solutions of the instant compositions within the 5 to 10 pH range in which peroxyacid bleaching agents are generally most useful. Depending upon the nature of other optional composition ingredients, pH adjustment agents can be either acidic or basic. Acidic pH adjustment agents (designed to compensate for the presence of other highly alkaline materials) include normally solid organic and inorganic acids, acid mixtures and acid salts. Examples of such acidic pH adjustment agents include citric acid, glycolic acid, tartaric acid, gluconic acid, glutamic acid, sulfamic acid, sodium bisulfate, potassium bisulfate, ammonium bisulfate and mixtures of citric acid and lauric acid. Citric acid is preferred by virtue of its low toxicity and hardness sequestering capability.

Optional alkaline pH adjustment agents include the conventional alkaline buffering agents. Such buffering agents include such salts as carbonates, bicarbonates, silicates, pyrophosphates and mixtures thereof. Sodium bicarbonate and tetrasodium pyrophosphate are highly preferred.

Optional peroxyacid bleach activators suggested by the prior art include such materials as aldehydes and ketones. Use of these materials as bleaching activators is described more fully in U.S. Pat. No. 3,822,114, issued July 2, 1974 to Montgomery, incorporated herein by reference.

Optional ingredients, if utilized in combination with the active peroxyacid of the instant invention to form a complete bleaching product, may comprise from about 20% to about 99% by weight of the total composition. Conversely, the peroxyacid compound made using the process of the present invention may comprise from about 1% to about 80% of the composition.

The bleaching compositions of the instant invention, particularly the dry granular version, can also be added to and made a part of conventional fabric laundering detergent compositions. Accordingly, optional materials for the instant bleaching compositions can include such standard detergent adjuvants as surfactants and builders. Optional surfactants are selected from the group consisting of organic anionic, nonionic, ampholytic, and zwitterionic surfactants and mixtures thereof. Optional builder materials include any of the conventional organic and inorganic builder salts including carbonates, silicates, acetates, polycarboxylates and phosphates. If the instant stabilized bleaching compositions are employed as part of a conventional fabric laundering detergent composition, the instant bleaching agent generally comprises from about 1% to about 40% by weight of such conventional detergent compositions. Conversely, the instant bleaching compositions can optionally contain from about 60% to about 99% by weight of conventional surfactant and builder materials.

Further examples of suitable surfactants and builders are given below.

Water-soluble salts of the higher fatty acids, i.e., "soaps," are useful as the anionic surfactant herein. This class of surfactants includes ordinary alkali metal soaps such as the sodium, potassium, ammonium and alkanolammonium salts of the higher fatty acids containing from about 8 to about 24 carbon atoms and preferably from about 10 to about 20 carbon atoms. Soaps can be made by direct saponification of fats and oils by the neutralization of free fatty acids. Particularly useful are the sodium and potassium salts of the mixtures of fatty acids derived from coconut oil and tallow, i.e., sodium or potassium tallow or coconut soaps.

Another class of anionic surfactants includes water-soluble salts, particularly the alkali metal, ammonium and alkanolammonium salts, of organic sulfuric reaction products having in their molecular structure an alkyl group containing from about 8 to about 22 carbon atoms and a sulfonic acid or sulfuric acid ester group. (Included in the term "alkyl" is the alkyl portion of acyl groups.) Examples of this group of synthetic surfactants which can be used in the present detergent compositions are the sodium and potassium alkyl sulfates, especially those obtained by sulfating the higher alcohols produced by reducing the glycerides of tallow or coconut oil; and sodium and potassium alkyl benzene sulfonates, in which the alkyl group contains from about 9 to about 15 carbon atoms in straight chain or branched chain configuration, e.g., those of the type described in U.S. Pat. Nos. 2,220,099, and 2,477,383, incorporated herein by reference.

Other anionic surfactant compounds useful herein include the sodium alkyl glyceryl ether sulfonates, especially those ethers or higher alcohols derived from tallow and coconut oil; sodium coconut oil fatty acid monoglyceride sulfonates and sulfates; and sodium or potassium salts of alkyl phenol ethylene oxide ether sulfates containing about 1 to about 10 units of ethylene oxide per molecule and wherein the alkyl groups contain about 8 to about 12 carbon atoms.

Other anionic surfactants useful herein include the water-soluble salts of esters of $\alpha$-sulfonated fatty acids containing from about 6 to 20 carbon atoms in the ester group; water-soluble salts of 2-acyloxy-alkane-1-sulfonic acids containing from about 2 to about 9 carbons atoms in the acyl group and from about 9 to about 23 carbon atoms in the alkane moiety; alkyl ether sulfates containing from about 10 to 24 carbon atoms in the alkyl group and from about 1 to 30 moles of ethylene oxide; water-soluble salts of olefin sulfonates containing from about 12 to 24 carbon atoms; and $\beta$-alkyloxy alkane sulfonates containing from about 1 to 3 carbon atoms in the alkyl group and from about 8 to 20 carbn atoms in the alkane moiety.

Preferred water-soluble anionic organic surfactants herein include linear alkyl benzene sulfonates containing from about 11 to 14 carbon atoms in the alkyl group; the tallow alkyl sulfates; the coconut alkyl glyceryl sulfonates; and alkyl ether sulfates wherein the alkyl moiety contains from about 14 to 18 carbon atoms and wherein the average degree of ethoxylation varies between 1 and 6.

Specific preferred anionic surfactants for use herein include: sodium linear $C_{10}$–$C_{12}$ alkyl benzene sulfonate; triethanolamine $C_{10}$–$C_{12}$ alkyl benzene sulfonate; sodium tallow alkyl sulfate; sodium coconut alkyl glyceryl ether sulfonate; and the sodium salt of a sulfated condensation product of tallow alcohol with from about 3 to about 10 moles of ethylene oxide.

It is to be recognized that any of the foregoing anionic surfactants can be used separately herein or as mixtures.

Nonionic surfactants include the water-soluble ethoxylates of $C_{10}$–$C_{20}$ aliphatic alcohols and $C_6$–$C_{12}$ alkyl phenols. Many nonionic surfactants are especially suitable for use as suds controlling agents in combination with anionic surfactants of the type disclosed herein.

Semi-polar surfactants useful herein include water-soluble amine oxides containing one alkyl moiety of from about 10 to 28 carbon atoms and 2 moieties selected from the group consisting of alkyl groups and hydroxyalkyl groups containing from 1 to about 3 carbon atoms; water-soluble phosphine oxides containing one alkyl moiety of about 10 to 28 carbon atoms and 2 moieties selected from the group consisting of alkyl groups and hydroxyalkyl groups containing from about 1 to 3 carbon atoms; and water-soluble sulfoxides containing one alkyl moiety of from about 10 to 28 carbon atoms and a moiety selected from the group consisting of alkyl and hydroxyalkyl moieties of from 1 to 3 carbon atoms.

Ampholytic surfactants include aliphatic derivatives of heterocyclic secondary and tertiary amines in which the aliphatic moiety can be a branched or straight chain and wherein one of the aliphatic substituents contains from about 8 to 18 carbon atoms and at least one aliphatic substituent contains an anionic water-solubilizing group.

Zwitterionic surfactants include derivatives of aliphatic quaternary ammonium, phosphonium and sulfonium compounds in which the aliphatic moieties can be straight or branched chains, and wherein one of the aliphatic substituents contains from about 8 to 18 carbon atoms and one of the aliphatic substituents contains an anionic water-solubilizing group.

The instant granular compositions can also comprise those detergency builders commonly taught for use in laundry compositions. Useful builders herein include any of the conventional inorganic and organic water-soluble builder salts, as well as various water-insoluble builders and so-called "seeded" builders.

Inorganic detergency builders useful herein include, for example, water-soluble salts of phosphates, pyrophosphates, orthophosphates, polyphosphates, phosphonates, carbonates, bicarbonates, borates and silicates. Specific examples of inorganic phosphate builders include sodium and potassium tripolyphosphates, phosphates, and hexametaphosphates. The polyphosphates also specifically include, for example, the sodium and potassium salts of ethylene diphosphonic acid, the sodium and potassium salts of ethane 1-hydroxy-1,1-diphosphonic acid, and the sodium and potassium salts of ethane-1,1,2-triphosphonic acid. Examples of these and other phosphorus builder compounds are disclosed in U.S. Pat. Nos. 3,159,581; 3,213,030; 3,422,021; 3,422,137; 3,400,176 and 3,400,148, incorporated herein by reference. Sodium tripolyphosphate is an especially preferred, water-soluble inorganic builder herein.

Nonphosphorus containing sequestrants can also be selected for use herein as detergency builders. Specific examples of nonphosphorus, inorganic builder ingredients include water-soluble inorganic carbonate, bicarbonate, borate and silicate salts. The alkali metal, e.g., sodium and potassium, carbonates, bicarbonates, borates (including borax) and silicates are particularly useful herein.

Water-soluble, organic builders are also useful herein. For example, the alkali metal, ammonium and substituted ammonium polyacetates, carboxylates, polycarboxylates, succinates, and polyhydroxysulfonates are useful builders in the present compositions and processes. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred nonphosphorous builder materials (both organic and inorganic) useful herein include sodium carbonate, sodium bicarbonate, sodium silicate, sodium citrate, sodium oxydisuccinate, sodium mellitate, sodium nitrilotriacetate, and sodium ethylene diamine tetraacetate, and mixtures thereof.

Another type of detergency builder material useful in the present compositions and processes comprises a water-soluble material capable of forming a water-insoluble reaction product with water hardness cations in combination with a crystallization seed which is capable of providing growth sites for said reaction product.

Specific examples of materials capable of forming such water-insoluble reaction products include the water-soluble salts of carbonates, bicarbonates, sesquicarbonates, silicates, aluminates and oxalates. The alkali metal, especially sodium, salts of the foregoing materials are preferred for convenience and economy.

Another type of builder useful herein includes various substantially water-insoluble materials which are capable of reducing the hardness content of laundering liquors, e.g., by ion-exchange processes. Examples of such builder materials include the phosphorylated cloths disclosed in U.S. Pat. No. 3,424,535, Bauman, issued Jan. 28, 1969, incorporated herein by reference.

The complex aluminosilicates, i.e., zeolite-type materials, are useful presoaking/washing adjuvants herein in that these materials soften water, i.e., remove $Ca^{++}$ hardness. Both the naturally occurring and synthetic "zeolites," especially zeolite A and hydrated zeolite A materials, are useful for this builder/softener purpose. A description of zeolite materials and a method of preparation appears in Milton, U.S. Pat. No. 2,882,243, issued Apr. 14, 1959, incorporated herein by reference.

A preferred dry, granular bleaching product employing the peroxyacid bleach of the present invention is made by combining the active peroxy compound with potassium aluminum sulfate or boric acid, the acid pyrophosphate/8-hydroxyquinoline chelating system, sodium sulfate, and linear alkyl benzene sulfonate, and subsequently coating this mixture with mineral oil.

COMPOSITION PREPARATON

The bleaching compositions of the instant invention are prepared in any conventional manner such as by admixing ingredients, by agglomeration, by compaction, by granulation, or by spray drying or prilling in the case of the dry granular form. A preferred method for forming the granular product is spray drying. The diperoxyacid and other components of the granule are thoroughly mixed in an agitated tank with sufficient water to form a smooth paste. This paste is atomized into the top of a conventional spray drying tower (either countercurrent air flow or cocurrent air flow) using a high pressure pump (500–1000 pounds per inch absolute, or $3.5 \times 10^5$ to $7.0 \times 10^5$ kg/m$^2$) and a nozzle setup. The atomized particles fall through the air stream which has been preheated to about 400° F. (200° C.) and are collected at the base of the tower. Inlet air conditions and product flow rate are adjusted to give an outlet air temperature of about 100°–150° F. (38°–66° C.) and a product moisture content of about 5% to 10%. One skilled in the art will recognize that these conditions are similar to those employed in spray drying any heat sensitive material such as powdered milk or the like. The spray dried granules are further dried in a mild, low temperature manner such as a fluid bed dryer with an inlet air temperature of 120°–140° F. (49°–60° C.). This two-stage drying operation yields a very dry granule which typically improves stability and minimizes activity losses during the drying operation.

Bleaching granules prepared in this manner can then be admixed with other granules of optional bleaching or detergent composition materials. The particle size of either the bleach-containing granules or optional granules of additional material is not critical. If, however, compositions are to be realized having commercially acceptable flow properties, certain granule size limitations are highly preferred. In general, all granules of the instant compositions preferably range in size from about 100 microns to 3000 microns, more preferably from about 100 microns to 1300 microns.

Additionally, flowability is enhanced if particles of the present invention are of approximately the same size. Therefore, preferably the ratio of the average particle sizes of the bleach-containing granules and optional granules of other materials has a value between 0.5:1 and 2.0:1.

Bleaching compositions of the present invention are utilized by dissolving them in water in an amount sufficient to provide from about 1.0 ppm to 100 ppm available oxygen in solution. Generally, this amounts to about 0.005% to 0.5% by weight of composition in solution. Fabrics to be bleached are then contacted with such aqueous bleaching solutions.

What is claimed is:

1. An improved continuous process for making a peroxyacid having about 6 to about 20 carbon atoms and at least one peroxyacid moiety, comprising the steps of:
   (a) Maintaining a reaction slurry comprising a liquid phase and a solid phase;
      i. Said liquid phase comprising 60 to 80% by mixture weight concentrated sulfuric acid, 2.5 to 12.5% by mixture weight hydrogen peroxide, and 7.5 to 37.5% by mixture weight water, and
      ii. Said solid phase comprising a peroxyacid having about 6 to about 20 carbon atoms and the carboxylic acid starting material corresponding to said peroxyacid;
   in a continuously stirred reaction vessel at a temperature between about 15 degrees Celsius and 45 degrees Celsius;
   (b) Continuously withdrawing from said stirred reaction vessel a first portion of said slurry and substantially removing said solid phase therefrom using filtration means, whereby to form a filtrate stream and a separate filter cake;
   (c) Mixing said filtrate stream with a quantity of hydrogen peroxide in water solution sufficient to maintain the hydrogen peroxide and water contents of said stirred reaction vessel, thereby forming a first reentering stream;

(d) Cooling said first reentering stream and inserting it into said stirred reaction vessel;

(e) Continuously withdrawing from said stirred reaction vessel a second portion of said slurry;

(f) Mixing said second portion of said slurry with sufficient quantities of said carboxylic acid starting material and said concentrated sulfuric acid to maintain the sulfuric acid and carboxylic acid starting material contents of said stirred reaction vessel, thereby forming a second reentering stream;

(g) Cooling said second reentering stream and inserting it into said stirred reaction vessel; and (h) Washing said filter cake to form a peroxyacid product;

whereby to continuously produce said peroxyacid product and remove it from said stirred reaction vessel while maintaining the composition and temperature of said slurry within the limits of step (a) hereof.

2. The invention of claim 1 wherein said peroxyacid has from about 8 to about 16 carbon atoms.

3. The process of claim 1 wherein the weight ratio of said liquid phase with respect to said solid phase is at least 3:1.

4. The process of claim 3 wherein the weight ratio of said liquid phase with respect to said solid phase is at least 8:1.

5. The process of claim 4 wherein the weight ratio of said liquid phase with respect to said solid phase is no more than about 50:1.

6. The process of claim 1 wherein said liquid phase comprises 70 to 77% by mixture weight sulfuric acid, 2.5 to 7.5% by mixture weight hydrogen peroxide, and 15.5 to 27.5% by weight water.

7. The process of claim 6 wherein said liquid phase comprises 71 to 75% by mixture weight sulfuric acid, 4.5% to 7.5% by mixture weight hydrogen peroxide, and 17.5% to 24.5% by mixture weight water.

8. The process of claim 7 wherein said solid phase contains about 92% of said peroxyacid and about 8% of said carboxylic acid starting material.

9. The method of claim 1 wherein said first reentering stream is cooled to a temperature which does not exceed about 35 degrees Celsius.

10. The method of claim 1 wherein said second reentering stream is cooled to a temperature which does not exceed about 35 degrees Celsius.

11. The process of claim 1 wherein said continuously stirred reaction slurry is maintained in said reaction vessel at a temperature of 32 to 35 degrees Celsius.

* * * * *